US012350400B1

(12) United States Patent
Hossain et al.

(10) Patent No.: US 12,350,400 B1
(45) Date of Patent: Jul. 8, 2025

(54) BIODEGRADABLE NANOCOMPOSITE SURGICAL SCREW CONTAINING BONE NANOPARTICLES

(71) Applicant: IMAM MOHAMMAD IBN SAUD ISLAMIC UNIVERSITY, Riyadh (SA)

(72) Inventors: A B M Sharif Hossain, Riyadh (SA); Hassan Ahmed Rudayni, Riyadh (SA); Mohammad Saad Aleissa, Riyadh (SA); Mohammed Musa Zahrany, Riyadh (SA); Abdulrahman Alhudhaibi, Riyadh (SA); Fazliny Abdul Rahman, Riyadh (SA)

(73) Assignee: IMAM MOHAMMAD IBN SAUD ISLAMIC UNIVERSITY, Riyadh (SA)

( * ) Notice: Subject to any disclaimer, the term of this patent is extended or adjusted under 35 U.S.C. 154(b) by 0 days.

(21) Appl. No.: 18/763,543

(22) Filed: Jul. 3, 2024

(51) Int. Cl.
| | | |
|---|---|---|
| *A61L 27/36* | (2006.01) | |
| *A61B 17/86* | (2006.01) | |
| *A61C 8/00* | (2006.01) | |
| *A61L 27/26* | (2006.01) | |

(52) U.S. Cl.
CPC ........ *A61L 27/3637* (2013.01); *A61B 17/866* (2013.01); *A61C 8/0028* (2013.01); *A61L 27/26* (2013.01); *A61L 27/3604* (2013.01); *A61L 27/3608* (2013.01); *A61L 27/365* (2013.01); *A61L 27/3691* (2013.01); *A61C 8/0012* (2013.01); *A61L 2400/12* (2013.01); *A61L 2430/02* (2013.01); *A61L 2430/12* (2013.01)

(58) Field of Classification Search
CPC .. A61L 27/3637; A61L 27/26; A61L 27/3604; A61L 27/3608; A61L 27/365; A61L 27/3691; A61L 2400/12; A61L 2430/02; A61L 2430/12; A61C 8/0028; A61C 8/0012; A61B 17/866
See application file for complete search history.

(56) References Cited

U.S. PATENT DOCUMENTS

| | | |
|---|---|---|
| 2010/0068297 A1 | 3/2010 | Naughton |
| 2012/0330366 A2 | 12/2012 | Al-Saidi et al. |

FOREIGN PATENT DOCUMENTS

| | | |
|---|---|---|
| CN | 107286602 B | 8/2020 |
| CN | 113164654 A | 7/2021 |

OTHER PUBLICATIONS

Salih et al. ; Investigation of Mechanical Properties of PMMA Composite Reinforced With Different Types of Natural Powders ; ARPN Journal of Engineering and Applied Science, vol. 13, No. 22 ; Nov. 2018 ; 12 Pages.
Bello et al. ; Development and Characterization of Date Seed Nanoparticles Reinforced Polylactic Acid (PLA) Nanocomposites ; Annals of Faculty Engineering Hunedoara—International Journal of Engineering ; May 2023 ; 8 Pages.
Soltazadeh et al. ; Active gelatin/cress seed gum-based films reinforced with chitosan nanoparticles encapsulating pomegranate peel extract: Preparation and characterization ; Food Hydrocolloids, vol. 129 ; Aug. 2022 ; 4 Pages.
Alara ; Okra Gel: Ultimate Hair and Skin Care Formula—Alara India ; https://alaraindia.com/products/okra-gel ; 22 Pages.
ASTM International ; Standard Test Method for Environmental Stress Crack Resistance (ESCR) of Threaded Plastic Closures ; Sep. 17, 2021 ; 2 Pages.
ASTM International ; Standard Test Method for Tensile Properties of Reinforced Thermosetting Plastics Using Straight-Sided Specimens ; Mar. 29, 2017 ; 3 Pages.
ASTM International ; Standard Test Method for Measuring the Comparative Burning Characteristics of Solid Plastics in a Vertical Position ; Sep. 11, 2020 ; 3 Pages.
ASTM International ; Standard Practice for Operating Salt Spray (Fog) Apparatus ; Dec. 10, 2019 ; 2 Pages.
ASTM International ; Standard Specification for Cold-Formed Welded and Seamless Carbon Steel Structural Tubing in Rounds and Shapes ; Aug. 16, 2017 ; 2 Pages.
ASTM International ; Standard Test Method for Performance of Exterior Windows, Curtain Walls, Doors, and Impact Protective Systems Impacted by Missile(s) and Exposed Cyclic Pressure Differentials ; Oct. 15, 2019 ; 3 Pages.
ASTM International ; Standard Test Method for Beam Deflection of "Fiberglass" (Glass-Fiber-Reinforced Thermosetting Resin) Pipe Under Full Bore Flow ; Aug. 15, 2019 ; 2 Pages.

*Primary Examiner* — Michael P Cohen
(74) *Attorney, Agent, or Firm* — Oblon, McClelland, Maier & Neustadt, L.L.P.

(57) ABSTRACT

A nanocomposite derived from organic sources, including waste date seeds, pomegranate peels and camel knee bone. The nanocomposites can be used for the synthesis of surgical implants, are biodegradable, and do not require surgery for their removal. The nanocomposites contain nanoparticles of date seeds, pomegranate peels, camel knee bone, polymers, organic substances, and organic dyes. A method for the preparation of the nanocomposites includes molding the nanocomposites into organic bone screws, bone plates, and dental prosthetics.

20 Claims, 4 Drawing Sheets

BIODEGRADABLE NANOCOMPOSITE SURGICAL SCREW CONTAINING BONE NANOPARTICLES

BACKGROUND

Technical Field

The present disclosure is directed to a biodegradable, nanocomposite derived from biobased organic sources, particularly from date seeds, pomegranate peels and camel bone for preparing surgical implants.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present invention.

Surgical implants, such as bone screws and plates, are commonly used in orthopedic surgeries for correcting bone defects or for the treatment of bone disorders and injuries resulting from accidents. These implants are generally made of metals, alloys, composites, polymeric substances, and ceramic materials. Implants made of stainless steel, titanium, cobalt-chromium, or magnesium alloys are frequently used that offer high strength and resistance to corrosion and possess superior biomechanical properties when compared to other implant materials.

Synthetic implants are often used to replace a damaged biological part or organ and improve the overall functionality of the body. However, these implants are not biodegradable and remain in the body if not removed by surgical intervention. Also, synthetic implants, if kept in the body for a longer duration of time, may sometimes pose risks and complications owing to compatibility issues with the surrounding organs or tissues. In such circumstances, the implants need to be removed by another surgery which is very laborious, time-consuming, costly, and sometimes dangerous for the patient.

Polymeric implants and composites based on modified polymers are often preferred because of their auto-degrading capabilities, which reduce the possibility of a second surgery to remove implants. However, these materials are not completely reliable as they have relatively lesser strength than synthetic implants and may react with the surrounding tissues, resulting in complications.

Ceramic implants are sometimes chosen because of their biodegradability and inert and non-toxic nature. Ceramic implants, especially bioceramics based on calcium phosphate, are preferred as their mineral composition resembles the composition of a natural bone. Although ceramic implants offer many advantages, they come with their own challenges especially reduction in their metallic strength and sometimes causing inflammation in the surrounding tissues.

Various other materials have been devised to prepare implants having improved properties and degradability. One such material is magnesium alloy, which is inert, biodegradable, and mimics the properties of a bone. Magnesium alloys are relatively fragile and brittle. Next in line are zirconium-based alloys, having higher strength and resistance against wear and tear, but the preparation of such implants involves higher synthesis costs, which makes them a less preferred choice.

Each of the aforementioned implant materials suffers from one or more drawbacks hindering their adoption, such as reactive nature, lesser mechanical strength, and non-biodegradability, requiring another surgical procedure for its removal. Accordingly, it is one object of the present disclosure to provide a nanocomposite material for medical and surgical dental purposes that is biodegradable, organic, biologically inert, and possesses superior mechanical strength.

SUMMARY

In an embodiment, an organic biodegradable nanocomposite for forming surgical implants is described. The organic biodegradable nanocomposite includes waste date seed nanoparticles present in an amount of about 15 wt. % to about 20 wt. %, pomegranate peel nanoparticles present in an amount of about 12 wt. % to about 16 wt. %, a polyvinyl chloride present in an amount of about 2 wt. % to about 5 wt. %, a polylactic glycolic acid present in an amount of about 2 wt. % to about 5 wt. %, an acrylate adhesive present in an amount of about 2 wt. % to about 5 wt. %, and a starch including a mixture of pure starch present in an amount of about 7 wt. %, the pomegranate peel nanoparticles present in an amount of about 5 to about 10 wt. % and the date seed nanoparticles present in an amount of about 5 to about 10 wt. %, a waste coconut gel present in an amount of about 2 wt. % to about 5 wt. %, a waste okra gel present in an amount of about 2 wt. % to about 5 wt. %, a fresh gum (*Lannea* sp.) present in an amount of about 2 wt. % to about 5 wt. %, *Acacia nilotica* gum present in an amount of about 2 wt. % to about 5 wt. %, a waste aroid gel present in an amount of about 2 wt. % to about 5 wt. %, a chicken gut oil-based glycerin present in an amount of about 5 to about 10 wt. %, a dragon fruit peel dye present in an amount of about 5 wt. % to about 10 wt. %, a pomegranate peel organic dye present in an amount of about 5 wt. % to about 10 wt. %, mangosteen peel organic dye present in an amount of about 3 wt. % to about 5 wt. % and the balance is the camel knee bone such that a total weight of the organic biodegradable nanocomposite is 100 wt. %, wherein wt. % is based on the total weight of the organic biodegradable nanocomposite.

In another embodiment, a method of making an organic biodegradable nanocomposite for use in forming a surgical implant is described. The method comprises pyrolyzing, by an oven, an amount of pomegranate peel; converting, by acid hydrolyzing in 88% hydrochloric acid, the pyrolyzed pomegranate peel to nanoparticles; grinding, in a grinder, an amount of date seeds to an average size ranging from 1 to 100 mm; converting, by acid hydrolysis in 88% hydrochloric acid, the ground date seeds to nanoparticles; converting, by acid hydrolysis in 90% hydrogen sulfate, camel knee bone to nanoparticles; combining the pomegranate peel nanoparticles, the date seed nanoparticles and the camel knee bone nanoparticles with an organic polymer; a mixture of organic substances; and an organic dye.

The foregoing general description of the illustrative embodiments and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

In the drawings, like reference numerals designate identical or corresponding parts throughout the several views. Further, as used herein, the words "a", "an" and the like generally carry a meaning of "one or more", unless stated otherwise.

Furthermore, the terms "approximately," "approximate", "about" and similar terms generally refer to ranges that include the identified value within a margin of 20%, 10%, or preferably 5%, and any values therebetween.

As used herein, "particle size" and "pore size" may be considered the lengths or longest dimensions of a particle and a pore opening, respectively.

As used herein, the term "degradation" refers to the removal of a substance from a system by breaking it down into chemically and/or physically smaller and easier-to-eliminate by-products and/or metabolites.

As used herein, the term "biodegradable" refers to any substance or material that can decompose and get resorbed into the environment, especially by the action of microorganisms.

As used herein, the term "organic" refers to a substance or material that can be produced from naturally occurring substances or materials.

As used herein, the term "nanocomposite" refers to a material having multiple phases embedded in a polymeric matrix wherein at least one of the phases comprises nanoparticles.

As used herein, the term "nanoparticles" refers to particles whose size ranges between 1 nm to 999 nm.

As used herein, the term "polymer" refers to a large molecule comprising a chain of smaller repeating units called monomers.

As used herein, the term "plasticizer" refers to substances added to a polymeric solution to incorporate plasticity and flexibility into the polymer.

As used herein, the term "curing" refers to a time in which a substance outgasses before a finished product can be obtained. Curing typically involves the application of a thermal heat profile, but the substance may also cure under ambient temperatures and pressures.

A weight percent of a component, unless specifically stated to the contrary, is based on the total weight of the formulation or composition in which the component is included. For example, if a particular element or component in a composition or article is said to have 5 wt. %, it is understood that this percentage is in relation to a total compositional percentage of 100 wt. %.

Aspects of the present disclosure are directed to biodegradable nanocomposites for forming surgical implants and, more particularly, to biodegradable nanocomposites formed from readily available organic sources, including pomegranate peel, camel bone, and date seeds. These organic sources are considered to be organic wastes and are often discarded or burned. These nanocomposites can be used to form surgical screws and compression plates that are required in surgery for bone fractures and can be used for both dental and medical purposes.

Aspects of the present disclosure describe a biodegradable nanocomposite for forming surgical implants including organic, biodegradable surgical screws, compression plates and dental prostheses. The nanocomposite includes starch nanoparticles obtained from any of pyrolyzed pomegranate peel and date seed waste. In an alternate embodiment, the pyrolyzed pomegranate peel can be at least partially replaced by mangosteen peel, depending on a desired dye color, cost or availability of the mangosteen peel. The nanocomposite further includes nanoparticles of camel knee bone, organic polymers, a mixture of organic substances and organic dyes.

In an aspect of the present disclosure, one or more polymers may be incorporated in the nanocomposite to provide sufficient mechanical strength, plasticity and flexibility. The polymers may serve to bind the nanocomposite into a desired shape of the implant. For example, the polymers may provide a rectangular, cylindrical, or spherical shape to the nanocomposite by molding. In certain aspects where the surgical implants are required in the form of screws or compression plates, the polymers may provide a similar shape to the nanocomposite by extrusion. Some polymers that are particularly useful in this regard may include polyvinyl chloride (PVC), polylactic acid, polyglycolic acid and polylactic glycolic acid (PLGA). Mixtures of polymers and polymer blends may be used as plasticizers to impart a desired strength, flexibility, and shape to the nanocomposite.

In one aspect, the polymer in the nanocomposite is polyvinyl chloride. In another aspect, the polymer in the nanocomposite is polylactic acid. In some aspects, the polymer in the nanocomposite is polylactic glycolic acid. In some aspects, the nanocomposite includes polyvinyl chloride in combination with polylactic glycolic acid. Such combination may include polyvinyl chloride in an amount of about 2 to about 5 wt. %, preferably about 3 wt. % to about 4 wt. % or about 3.5 wt % and polylactic glycolic acid in an amount of about 2 wt. % to about 5 wt. %, about 3 wt. % to about 4 wt. %, preferably about 3.5 wt %. In a preferred aspect, the nanocomposite may include polyvinyl chloride in an amount of about 3 wt. % and polylactic glycolic acid in an amount of about 3 wt. %.

The nanocomposite includes an adhesive for bonding the components of the nanocomposite. The adhesive provides additional strength to the nanocomposite. In a specific aspect, the adhesive is based on a polymeric resin. The polymeric resin is used to form a strong bond with the polymers and biomaterials. The polymeric resin may include an acrylic polymer as an adhesive. In some aspects, an acrylate adhesive may be present in an amount of about 2 wt. % to about 5 wt. %, preferably about 3 wt. % to about 4 wt. %, preferably about 3 wt. %.

In certain aspects, the nanocomposite includes polyvinyl chloride, polylactic glycolic acid, and acrylate adhesive in a combination wherein each is present in an amount of about 3 wt. %.

The nanocomposite includes a starch source wherein the starch source is a biobased material. The biobased materials include naturally occurring, renewable sources and may be of plant or animal origin. In certain aspects, the starch source is a plant-based source. In a specific aspect, the plant-based sources may include seeds of date fruits and peels of pomegranate fruits. In one aspect, the starch source is seeds of date fruit. Date fruits can be obtained from date palm trees and are used for therapeutic purposes owing to their anti-oxidant and anti-microbial properties. The seeds of date fruit have high starch content which is around 60-70% of the total content of various components present in the seed.

Date seed and pomegranate peel have starch in abundance. With the increasing environmental awareness and the growing importance of organic materials, plant-based starch has also been innovatively recognized for all its organic properties, and its applications are being recognized in other fields, too, such as medical, dental, biomedical, and bioengineering industries. The present disclosure utilizes these properties of date seed and pomegranate peel to explore innovative surgical nanocomposite biomaterials (bioscrew and compression plate) for medical and dental surgical uses. In addition, it can be produced commercially in the biomedical, medical, and dental industries.

Pomegranate peel nanoparticles are added to provide the desired starch content to the nanocomposite. Pomegranate peel contains bioactive compounds, including tannins, starch, cellulose, lignin and pectin. Pomegranate rinds are also useful in dyeing. Immature fruits yield pale yellow dyes, while ripe fruits yield golden yellow dyes.

In one aspect, the biobased starch in the nanocomposite is derived from combinations of nanoparticles formed from pomegranate peels and the seeds of date fruit. In a preferred aspect, the starch derived from pomegranate peel and date seed may be present in an amount in a range of about 10 wt. % to about 20 wt. %, a range of about 12 wt. % to about 16 wt. %, a range of about 13 wt. % to about 15 wt. %, preferably an amount of 13.26 wt. %. In one aspect, the starch derived from nanoparticles of pomegranate peel may be present in an amount of about 4 wt. % to about 7 wt. %, about 5 wt. % to about 6 wt. %, preferably about 5.68 wt. % and the amount of starch derived from nanoparticles of date seed is preferably about 7.68 wt. %. An additional amount of pure starch was added in an amount of 7 wt. %.

In certain aspects, the total amount of polyvinyl chloride, polylactic glycolic acid, the acrylate adhesive, and the starch in the nanocomposite is about 14-17 wt. %. In some aspects, the total amount of polyvinyl chloride, polylactic glycolic acid, the acrylate adhesive, and the starch in the nanocomposite is about 15 wt. %, preferably about 16 wt. %, preferably about 17 wt. %. In a specific aspect, the total amount of polyvinyl chloride, polylactic glycolic acid, the acrylate adhesive, and the starch in the nanocomposite is about 17 wt. %.

The pomegranate peels are converted to nanoparticles to prepare the nanocomposite. In a preferred aspect, the nanoparticles of the peels of pomegranate may be present in an amount of about 12 wt. % to about 16 wt. %. In one aspect, the pomegranate peel nanoparticles may be present in an amount of about 13 wt. % to about 16 wt. %, preferably about 14 wt. % to about 16 wt. %. In a specific aspect, the pomegranate peel nanoparticles may be present in an amount of about 14 wt. % to about 15 wt. %. In a preferred aspect, the pomegranate peel nanoparticles may be present in an amount of about 14.1 wt. %.

The nanocomposite includes nanoparticles obtained from waste date seeds. The nanoparticles from waste date seeds may be present in an amount of about 15 wt. % to about 20 wt. %. In one aspect, the date seed nanoparticles may be present in an amount of about 16 to about 20 wt. %, preferably about 17 wt. % to about 20 wt. %, preferably about 18 wt. % to about 20 wt. %. In a specific aspect, the date seed nanoparticles may be present in an amount of about 18 wt. % to about 19 wt. %. In a preferred aspect, the date seed nanoparticles may be present in an amount of about 18.8 wt. %.

The nanocomposite further includes nanoparticles derived from bone of an animal. In certain aspects, the nanocomposite includes nanoparticles derived from knee bone of an animal. In a preferred aspect, the nanoparticles are derived from knee bone of a camel. The camel knee bone is crushed to form a powder and the particles in the powder are converted to nanoparticles by acid hydrolysis. In one aspect, the nanocomposite includes camel knee bone nanoparticles in an amount of about 12 wt. % to about 15 wt. %. In certain aspects, the nanocomposite includes camel knee bone nanoparticles in an amount of about 13 wt. % to about 15 wt. %, preferably about 14 wt. % to about 15 wt. %. In a preferred aspect, the nanocomposite includes the camel knee bone nanoparticles in an amount of about 14.1 wt. %.

The nanocomposite of the present disclosure further includes a mixture of organic substances in an amount of about 2 wt. % to about 10 wt. %. The organic substances include waste coconut gel, waste okra gel, fresh gum obtained from *Lannea* sp., gum from *Acacia nilotica*, waste aroid gum, and chicken gut oil-based glycerine. Coconut gel is obtained from fermentation of coconut water by bacteria. The bacteria *Komagataeibacter xylinus* is known to produce cellulose, particularly bacterial cellulose. The coconut water is extracted from a tender coconut and subjected to fermentation by *Komagataeibacter xylinus*. The coconut gel so obtained is used as an ingredient in the production of various food products. The residual gel left after the production process is discarded as waste by the industries. The waste coconut gel can be used in the nanocomposite of the present disclosure. In some aspects, the nanocomposites include the waste coconut gel in an amount of about 2 wt. % to about 5 wt. %. In one aspect, the waste coconut gel is present in the nanocomposite in an amount of about 3 wt. % to about 4 wt. %.

Another organic substance that can be used in the present nanocomposite is okra gel made from okra waste. Okra gel can cause platelet activation at the wound site and further strengthen its hemostatic performance. It is biocompatible, biodegradable, and can promote wound healing and shows potential as a sustainable bioadhesive, especially in the scenario of significant hemorrhage, such as in the placement of bone screws and plates. Okra gel can be obtained from different parts of okra plants including the stems and leaves. During post harvesting of okra fruits, the okra plants are collected as agro-waste. These okra plants can be used for the extraction of gel that includes high amounts of pectins and carbohydrates. In some aspects, the nanocomposites include okra gel in an amount of about 2 wt. % to about 5 wt. %. In one aspect, the okra gel is present in the nano-composite in an amount of about 3 wt. % to about 4 wt. %. Okra gel can be made in a laboratory by boiling okra until soft, straining the mixture and cooling. In an aspect, the okra gel was made by obtaining waste okra, i.e., that which is rotten or unmarketable, grinding the waste okra, sieving the ground waste okra to collect the mucilaginous substances, which responsible for forming the okra gel, heating and stirring with 30% water. After cooling, 30% ethanol was added. Okra gel is a mucilage comprising polysaccharides consisting of glucose, arabinose, galactose, xylose, mannose and rhamonose, and glucuronic acid. In an aspect, okra get can be obtained commercially as a product "Okra Gel" manufactured by Alara India, Gujarat, India.

The organic substances in the nanocomposite further include plant-derived gums and gels. The plant-derived gums and gels include natural glue or fresh gum obtained from the plant *Lannea* sp., gum obtained from the plant *Acacia nilotica*, and gel obtained from aroid plants, including *Anthurium, Alocasia*, and philodendrons. The natural gums and gels are particularly useful as they contain high amounts of polysaccharides, are water soluble and biodegradable. In some aspects, the nanocomposites include fresh gum from *Lannea* sp. in an amount of about 2 wt. % to about 5 wt. %. In some aspects, the nanocomposites include fresh gum from *Lannea* sp. in an amount of about 3 wt. % to about 4 wt. %. In certain aspects, the nanocomposites include gum obtained from plant *Acacia nilotica* in an amount of about 2 wt. % to about 5 wt. %. In specific aspects, the nanocomposites include gum from plant *Acacia nilotica* in an amount of about 3 wt. % to about 4 wt. %, preferably about 3.5 wt. %. *Acacia nilotica* is commonly referred to as Gum Arabic and can be purchased commercially from a pharmacy.

In certain aspects, the nanocomposites include waste aroid gel in an amount of about 3 wt. % to about 8 wt. %. In specific aspects, the nanocomposites include waste aroid gel in an amount of about 4 wt. % to about 7 wt. %, about 5 wt. % to about 6 wt. %, preferably about 5.5 wt. %.

The nanocomposites further include glycerin derived from chicken fat, particularly from chicken gut. Glycerin is highly soluble in water and enhances the degradability of a polymer when added as a plasticizing agent. In certain aspects, the nanocomposites include chicken gut oil-based glycerin in an amount of about 5 wt. % to about 10 wt. %. In specific aspects, the nanocomposites include chicken gut oil-based glycerin in an amount of about 5 wt. % to about 10 wt. %, preferably about 6 wt. % to about 9 wt. %, preferably about 7 wt. % to about 8 wt. %.

Chicken gut oil-based glycerin was synthesized in the laboratory from waste chicken parts, such as the crop, gizzard, proventriculus, gizzard, duodenum, jejunum, ileum, caeca, large intestine, and cloaca. The process used to obtain glycerin from the chicken gut includes obtaining the waste chicken gut from a source, such as a chicken slaughtering house, washing the waste chicken gut, heating in an oven at 80° C. for 5 hours, cooling and extracting the oil. Glycerin was prepared from the chicken gut oil by adding methanol in a ratio of one part methanol to six parts chicken gut oil, adding a catalyst such as sodium hydroxide (NaOH) in a ratio of about 15 g NaOH per 100 g chicken gut oil, shaking, in a commercial shaker, for three hours at a temperature of about 40° C. After settling, the glycerin fell to the bottom of the shaker and was separated from an upper layer of methyl ester.

In a preferred aspect, the nanocomposite includes coconut gel in an amount of about 4 wt. %, okra gel in an amount of about 3 wt. %, fresh gum in an amount of about 3 wt. %, *Acacia nilotica* gum in an amount of about 3 wt. %, waste aroid gel in an amount of about 5 wt. %, and chicken gut oil-based glycerin in an amount of about 6 wt. %.

The waste aroid gel was prepared by peeling the waste aroid, boiling the peeled waste aroid for one hour in distilled water, in a ratio of 30% distilled water to 70% peeled waste aroid, crushing the boiled waste aroid to extract an aroid paste, adding 30% ethanol to 70% aroid paste, simmering the mixture while stirring to form the waste aroid gel. The waste aroid gel contains mucilage as a polysaccharide which acts as a biocompatible adhesive in the polymer mixture which increases the plasticity.

*Lannea* genus is a bush or tree widely distributed in tropical Africa and Asia, which is a genus in the cashew family (Anacardiaceae). Species of the *Lannea* genera are used to treat medical symptoms such as ulcers, enteritis, diarrhea, dysentery and rheumatism. The *Lannea* genera have antimicrobial, antioxidant, anti-inflammatory, and cytotoxic activities. The fresh gum from *Lannea* sp. was prepared by gathering fresh gum from a *Lannea* tree, adding water in a ratio of 30% water to 70% fresh gum, simmering and stirring for one hour and cooling to extract the fresh gum. The fresh gum contains polysaccharides, which acts as a biocompatible adhesive in the polymer mixture.

The nanocomposite includes organic dyes to impart natural color to the implants. In some aspects, the nanocomposites utilize pigments from the peels of dragon fruits, pomegranates and or mangosteen to acquire same color as that of the muscles and tissues surrounding the bone to be corrected. The peels of dragon fruit have a red-purple color, which is due to the presence of betacyanins in the peels. Pomegranate peels are dark red in color, and the color is imparted by the pigments, anthocyanins, and ellagitannins. Mangosteen peels contain a natural dye in the form of anthocyanins which generally produce red, purple, and blue colors.

Mangosteen fruit is an edible fruit obtained from the mangosteen tree. Mangosteen trees are tropical trees cultivated in warmer regions such as Southeast Asia. Mangosteen fruit is known for its medicinal properties, having antimicrobial, anti-inflammatory, and anti-parasitic functions. The fruit peel also has a high starch content of about 28-30% of the content of other components present in the peel. Mangosteen peels also contain a number of pigments that come from two metabolites, namely mangostin and β-mangostin. If all of the content contained in the mangosteen fruit is extracted, natural dye can be obtained in the form of anthocyanins which generally produce red, purple, and blue colors.

In certain aspects, the nanocomposites include organic dye present in an amount of about 9 wt. % to about 14 wt. %, preferably about 12 wt. %. In some aspects, the nanocomposites include dragon fruit peel dye in an amount of about 4 wt. %. A desired color of the nanocomposite can be obtained by mixing the organic dyes obtained from combinations of the pomegranate peel dye in an amount of about 4 wt. %, dragon fruit dye in an amount of about 4 wt. % and mangosteen peel dye in an amount of about 4 wt. %.

In certain aspects, the nanocomposites include organic dye obtained from pomegranate peels wherein the dye is present in an amount of about 5 wt. % to about 10 wt. %, about 6 wt. % to 9 wt. %, about 7 wt. % to about 8 wt. %, preferably about 7 wt. %. In some aspects, the total amount of dragon fruit peel dye and pomegranate peel dye in the nanocomposite is about 10 wt. % to about 13 wt. %, preferably about 12 wt. %. In a preferred aspect, where the total amount of dragon fruit peel dye and pomegranate peel dye is about 12 wt. %, the dragon fruit peel dye is present in an amount of about 6 wt. %, and the pomegranate peel dye is present in an amount of about 6 wt. %.

Referring to FIG. 1 and FIG. 2A-2J, a method 100 of making an organic biodegradable nanocomposite is described. The order in which the method 100 is described is not intended to be construed as a limitation, and any number of the described method steps can be combined in any order to implement the method 100. Additionally, individual steps may be removed or skipped from the method 100 without departing from the spirit and scope of the present disclosure.

Figure 1:
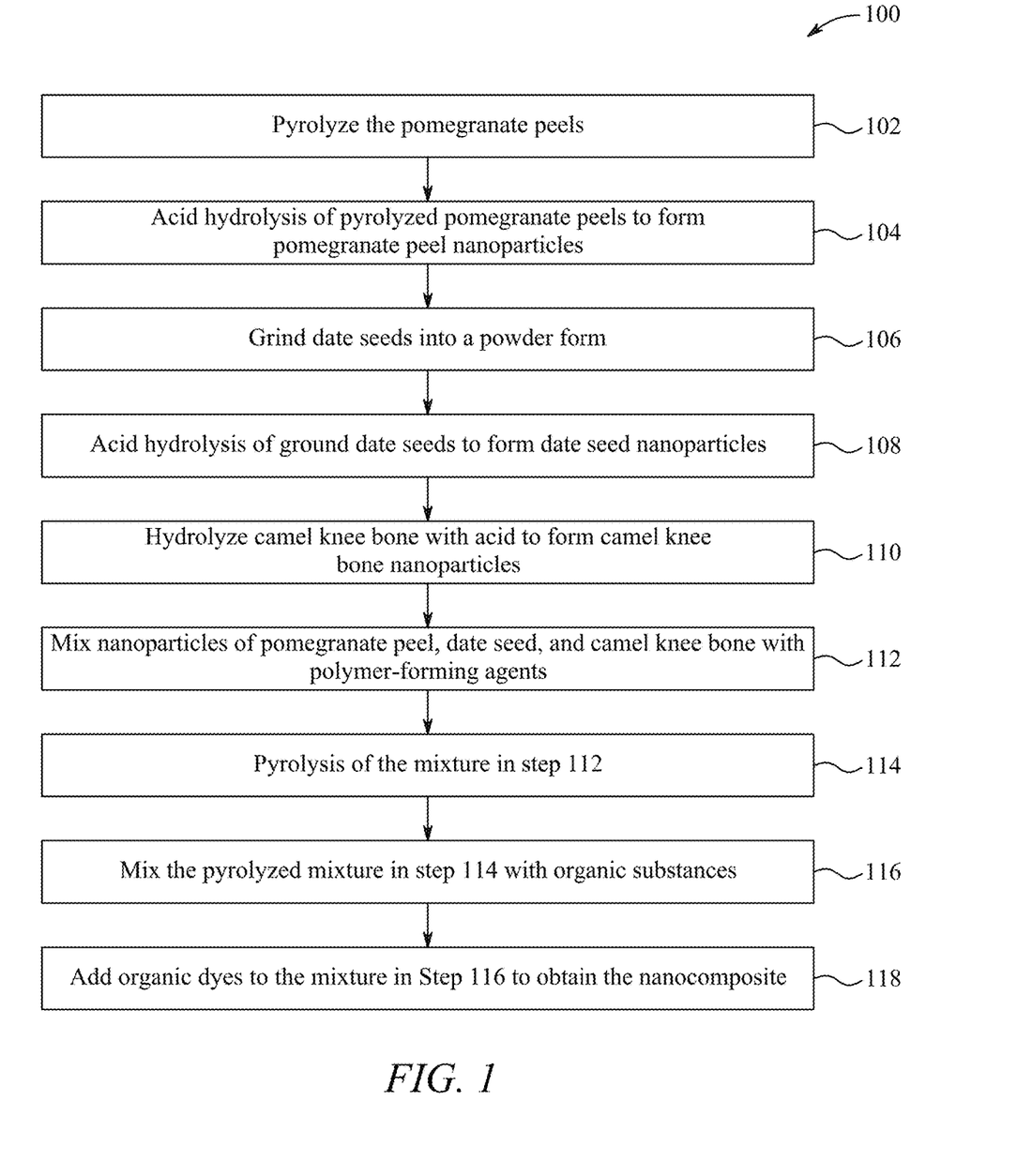
FIG. 1 is a flowchart depicting a method of preparation of organic biodegradable nanocomposites, according to certain embodiments.
Figure 2A:
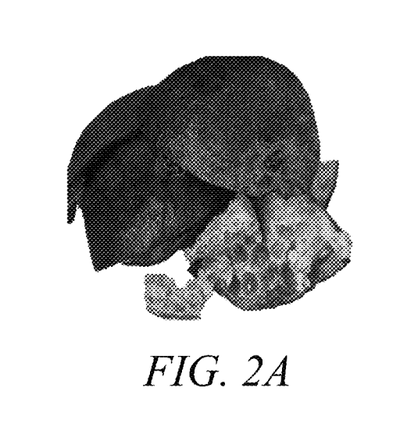
FIG. 2A is a pictorial image of a pomegranate peel, according to certain embodiments.
Figure 2B:
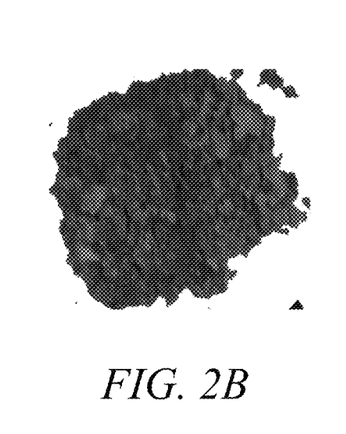
FIG. 2B is a pictorial image of the pomegranate peel ground into a powder, according to certain embodiments.
Figure 2C:
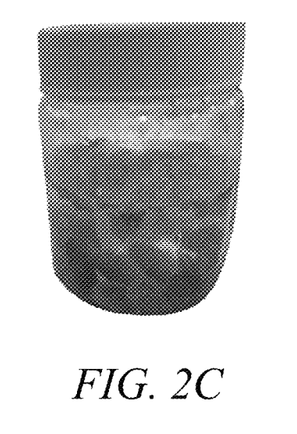
FIG. 2C is a pictorial image of a waste date seed, according to certain embodiments.

At step 102, the method 100 includes heating the pomegranate peels at a high temperature by a process called pyrolysis. In some aspects, prior to heating, the pomegranate peels (FIG. 2A) are ground into a fine powder (FIG. 2B). The pomegranate peels/powder is subjected to decomposition in an inert environment at temperatures of about 120° C. to about 130° C. In some aspects, the pomegranate peels are heated at temperatures of about 121° C., preferably about 123° C., preferably about 125° C., preferably about 127° C., preferably about 129° C., preferably about 130° C. The heating can be performed in suitable equipment, which may be selected from reactors, including rotary kiln reactors, fluidized bed reactors, pyrolysis reactors, microwave pyrolysis reactors, or an oven. In a specific aspect, the pomegranate peels are heated in an oven at 130° C. for a period of about 3 to 4 hours, preferably for a period of about 3.5 hours.

At step 104, the method 102 includes converting pyrolyzed pomegranate peels into nanoparticles. The pyrolyzed pomegranate peels are subjected to hydrolysis by an acid. The acid may be hydrochloric acid (HCl) or sulfuric acid ($H_2SO_4$). In a specific aspect, the pyrolyzed pomegranate peels are hydrolyzed by hydrochloric acid. The concentration of HCl may be about 85-90%. In some aspects, the concentration of HCl may be about 86%, 87%, 88% or 89%. In a preferred aspect, the concentration of HCl may be about 88%.

Figure 2D:
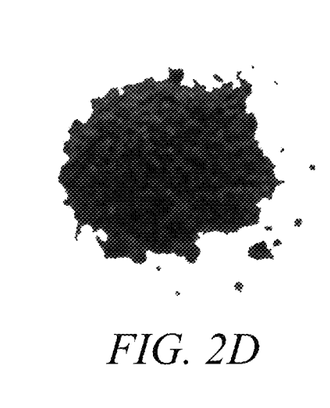
FIG. 2D is a pictorial image of the waste date seed ground into a powder, according to certain embodiments.
Figure 2E:
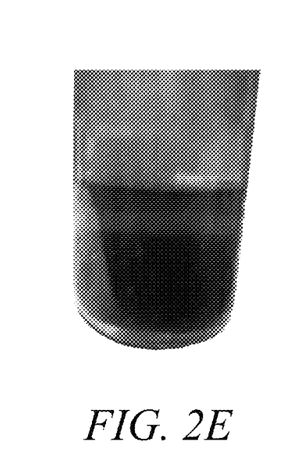
FIG. 2E is a pictorial image showing acid hydrolysis of the waste date seed powder into nanoparticles, according to certain embodiments.
Figure 2F:
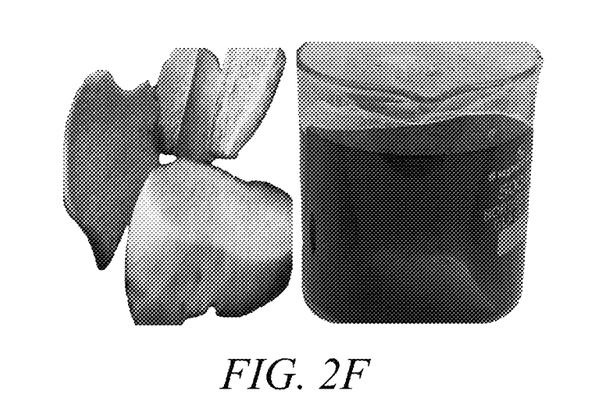
FIG. 2F is a pictorial image of camel knee bone and submersion of the camel knee bone into an acid hydrolysis solution, according to certain embodiments.

At step 106, the method 100 includes grinding date seeds (FIG. 2C) to convert date seeds to a powder form (FIG. 2D). The date seeds, preferably waste date seeds are ground in a date seed grinder or a mill machine to a powder form. The grinding of the date seeds is continued until a particle size of about 1 to 100 mm is achieved. In some aspects, the particle size of the ground date seeds is about 10 mm to 90 mm, preferably about 20 mm to 80 mm, preferably about 30 mm to 70 mm, preferably about 40 mm to 60 mm, preferably about 50 mm.

At step 108, the method 100 includes converting the ground date seeds into nanoparticles. The ground date seeds are hydrolyzed by an acid (FIG. 2E) which may be selected from hydrochloric acid (HCl) or sulfuric acid ($H_2SO_4$). In some aspects, the ground date seeds are hydrolyzed by hydrochloric acid. In some aspects, the ground date seeds are hydrolyzed by about 85% to about 90% hydrochloric acid. In other aspects, the ground date seeds are hydrolyzed by about 86% to about 88% hydrochloric acid. In a preferred aspect, the ground date seeds are hydrolyzed by about 88% hydrochloric acid.

Figure 2G:
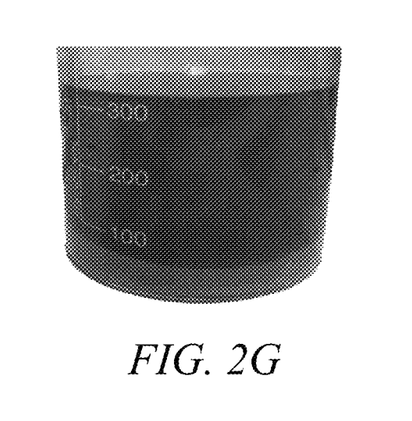
FIG. 2G is a pictorial image showing camel knee bone reduced to nanoparticles, according to certain embodiments.

At step 110, the method 100 includes grinding the camel knee bone (left side of FIG. 2F) to a powder form. The grinding of camel knee bone can be performed in a bone grinder or milling machine. The ground camel knee bone is then subjected to acid hydrolysis (right side of FIG. 2G). The camel knee bone powder is hydrolyzed by an acid, which may be sulfuric acid. The concentration of sulfuric acid may be about 85% to about 90%. In some aspects, the concentration of sulfuric acid may be about 87 to 90%. In other aspects, the concentration of sulfuric acid may be about 89% to about 90%. In a preferred aspect, the ground camel knee bone is hydrolyzed by 90% sulfuric acid. The acid hydrolysis process converts the bone to nanoparticles (FIG. 2G).

Figure 2H:
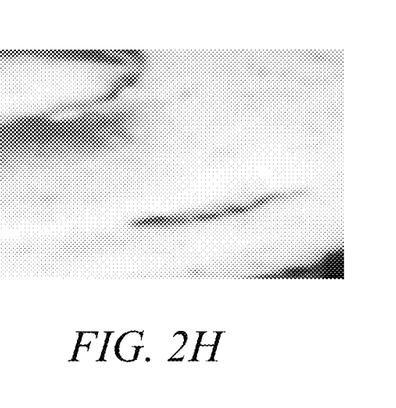
FIG. 2H is a pictorial image of a plasticizer mixture in an initial stage, according to certain embodiments.
Figure 2I:
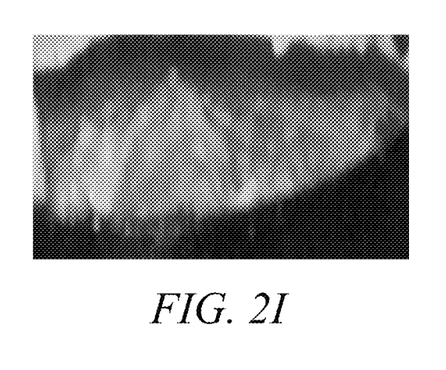
FIG. 2I is a pictorial image of the plasticizer mixture in its final stage, according to certain embodiments.

At step 112, method 100 includes mixing the nanoparticles of pomegranate peel, date seed, and camel knee bone with the polymer-forming agents. The polymers, including polyvinyl chloride, polylactic glycolic acid, acrylate adhesive, and starch from mangosteen peels and date seeds, are mixed with the nanoparticles along with water. The water may be tap water, ionized water, distilled water, or reverse osmosis water. In certain aspects, the water is distilled water. In a preferred aspect, the water is 20% distilled water. In one aspect, about 14.1 wt. % of pomegranate peel nanoparticles, about 18.8 wt. % of date seed nanoparticles and about 14.1% wt. % of the camel knee bone nanoparticles were mixed with about 3 wt. % of polyvinyl chloride, about 3 wt. % of a polylactic glycolic acid, about 3 wt. % of an acrylate adhesive and about 7 wt. % of a pure starch. The mixing can be done in a blender. In one aspect, the blending of the mixture is carried out for a period of 5-10 min to allow proper mixing of the components (FIG. 2H).

At step 114, the method 100 includes subjecting the mixture of polymers and nanoparticles to heating and/or pyrolysis, preferably at temperatures of 120° C. to about 135° C. In some aspects, the mixture is heated at temperatures in ranges of about 122° C. to about 135° C., about 124° C. to about 135° C., about 126° C. to about 132° C., about 128° C. to about 132° C., preferably about 130° C. The heating may be carried out in a reactor or an oven for a period of about 15 min. to about 25 min. In some aspects, the heating may be carried out for a period of about 16 minutes to about 24 min, for a period of about 17 min. to about 23 min, for a period of about 18-22 min., for a period of about 19-21 min., preferably for a period of about 20 min.

At step 116, the method 100 includes adding a mixture of organic substances to the heated/pyrolyzed mixture of polymer-forming agents and the nanoparticles. The organic substances, including coconut gel, waste okra gel, natural glue, *Acacia nilotica* gum, waste aroid gel, and chicken gut oil-based glycerin, are added to the heated/pyrolyzed mixture. In some aspects, about 4 wt. % of a coconut gel, about 3 wt. % of an okra gel, about 3 wt. % of a natural glue made from fresh gum of a *Lannea* species, about 3 wt. % of an

*Acacia nilotica* gum, about 5 wt % of an aroid gel and about 6 wt. % of an oil-based glycerin derived from the chicken gut are mixed with the pyrolyzed mixture followed by pyrolyzing the entire mixture for a period of about 5 to 15 min. The pyrolysis is carried out for a period of about 7 min. to 13 min, preferably 9 min. to 11 min, preferably for a period of 10 min. In certain aspects, the pyrolysis is carried out until the mixture appears plasticized (FIG. 2I) and a biopolymer is obtained.

Figure 2J:
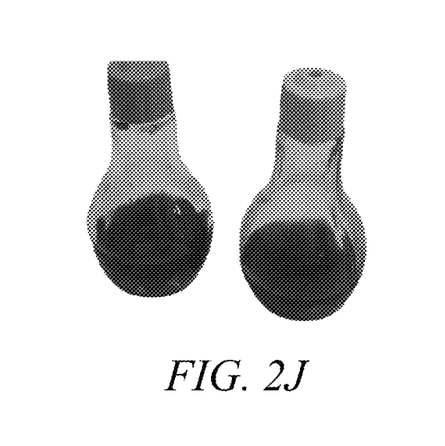
FIG. 2J is a pictorial image of a colored solution (dye) obtained on the extraction of the powder of the pomegranate peel/dragon fruit peel/mangosteen peel, according to certain embodiments.

At step 118, the method 100 includes mixing the organic peel dyes with the bio-polymer to impart a natural red color to the biopolymer. The organic peel dyes include any of pomegranate peel dye, mangosteen peel dye and dragon fruit peel dye (FIG. 2J). In an example, about 6 wt. % of a dragon fruit peel dye and about 6 wt. % of a pomegranate peel dye are added to the biopolymer. The mixing can be done either manually or with the help of a stirrer. The dyes are mixed with the biopolymer for a period of about 5 min. to about 10 min to obtain the biodegradable organic nanocomposite according to the present disclosure.

Figure 2K:
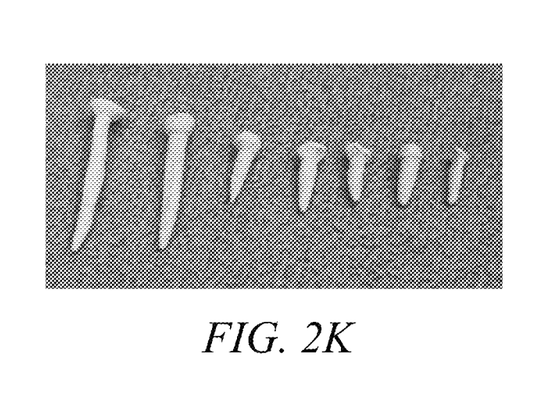
FIG. 2K is a pictorial image of an organic, biodegradable screw obtained by the methods of present disclosure, according to embodiments.
Figure 2L:
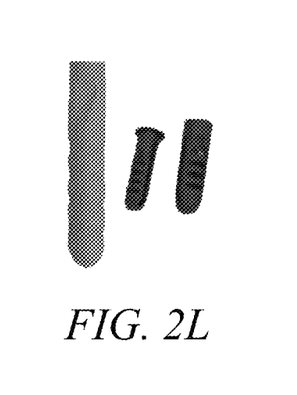
FIG. 2L is a pictorial image of different screw dice, according to certain embodiments.

The nanocomposite obtained from method 100 can be molded to form surgical implants. In some aspects, the surgical implants prepared from the nanocomposite include bone screws, bone plates, and dental prosthetics. The implants can be prepared by any of an extrusion molding process, an injection molding process and by pressing into a mold. Before the molding process begins, the molds are swabbed with an oil for easy release of the implant. In certain aspects, the oil is olive oil. In certain aspects, a bone screw is prepared by extrusion molding of the nanocomposite, wherein the nanocomposite is in a plasticized liquid form. The nanocomposite liquid is passed through a mold having the shape of a bone screw and is constantly pushed to achieve a polymer of the desired shape. Once a bone screw is formed, the mold is heated to obtain the cured bone screw (FIG. 2K). A fan heater (small fan with dryer) was used dry the mold for settling and cooling down for an 8 hour period. FIG. 2L shows different sized bone screw dice.

Figures 2M, 2O:
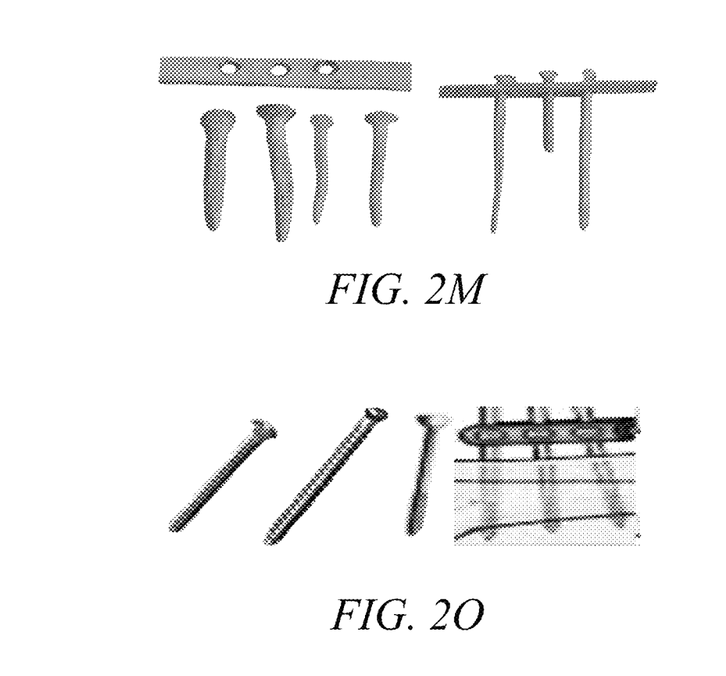
FIG. 2M is a pictorial image of the biodegradable, organic screw and plate, according to certain embodiments.
FIG. 2O is a pictorial image of conventional steel screws and steel surgical plates.
Figure 2N:
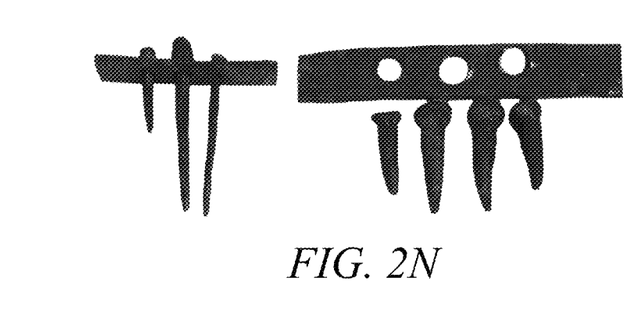
FIG. 2N is a pictorial image of the biodegradable, organic screw and plate after the addition of the dye, according to certain embodiments.

In some aspects, a bone plate is prepared by injection molding of the nanocomposite. The nanocomposite is in a plasticized liquid form which is then injected into a mold having the shape of a compression plate, followed by curing of the mold to obtain the bone plate (FIG. 2M). A dental prosthetic, for example, a dental post to support a tooth implant, such as a temporary crown or temporary post, can also be prepared by injection molding of the nanocomposite of the present disclosure. The nanocomposite in a plasticized liquid form is injected into a dental prosthetic mold. Once the prosthetic is formed, it is removed and washed with a solvent to remove the oil from the implants. The solvent is preferably an organic solvent. Suitable examples of organic solvents include polyethylene glycol, methylene glycol, tri-ethylene glycol, and ethylene glycol. The nanocomposite may be mixed with the organic dyes to form products of a desired color (FIG. 2N).

After the molding process, the implants are subjected to drying at temperatures of about 70° C. to about 90° C. In some aspects, the implants are heated at temperatures of about 75° C. to about 85° C., preferably at temperatures of about 80° C. The implants may be heated in an oven for a period of about 10 min. to about 15 min, followed by hardening at temperatures of about −3° C. to about −6° C., about −4° C. to about −6° C., preferably at temperatures of about −5° C.

FIG. 2O is a pictorial image of conventional steel screws and steel surgical plates.

Figure 2P:
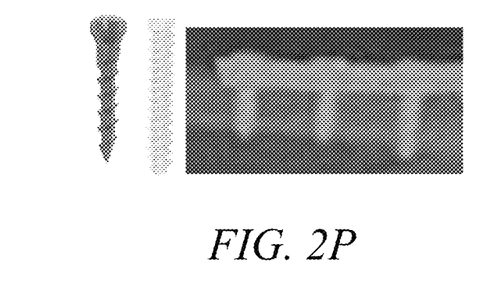
FIG. 2P is a pictorial image of conventional synthetic surgical screws and plates.

FIG. 2P is a pictorial image of conventional synthetic surgical screws and plates.

Figure 2Q:
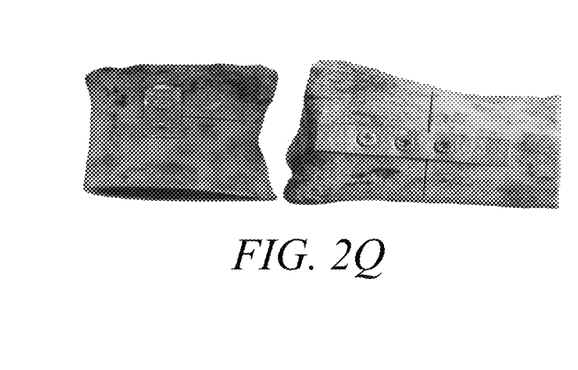
FIG. 2Q is a pictorial image of conventional steel screws and a steel surgical plates fixed in fresh cow bone.

FIG. 2Q is a pictorial image of conventional steel screws and a steel surgical plates fixed in fresh cow bone.

Figure 2R:
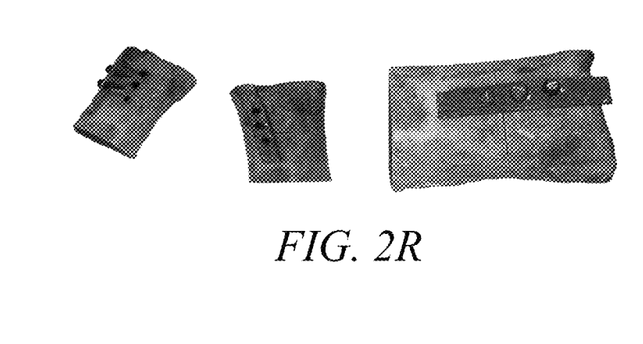
FIG. 2R is a pictorial image of the biodegradable organic screw and the plate after the addition of the dye fixed in fresh cow bone, according to certain embodiments.

FIG. 2R is a pictorial image of the biodegradable organic screw and the plate after the addition of the dye fixed in fresh cow bone.

EXAMPLES

The following examples demonstrate the preparation of nanocomposites and the surgical implants as described herein. The examples are provided solely for illustration and are not to be construed as limitations of the present disclosure, as many variations thereof are possible without departing from the spirit and scope of the present disclosure.

Example 1: pH and Starch Determination

The pH and cellulose content of the starch of the nanobioscrew of the present disclosure were determined, and their values were compared to those of surgical synthetic screws available in the market. As used herein, the "nanobioscrew" refers to the screw made from the nanocomposite derived from biobased sources of the present disclosure. The term "nanobioscrew" may also be referred to as the biodegradable, organic screw or the organic bone screw. The pH was determined using a Horiba Scientific pH meter, Japan. The quantitative determination of starch was carried out using methods known in the art. The results of this test are depicted in Table 1.

TABLE 1 pH and nanostarch determination

| Materials | pH Determination | Starch Determination |
|---|---|---|
| Nanobioscrew | 7.7 ± 0.03 | 40.3% ± 0.1 |
| Surgical synthetic screw | Alkaline ≥ 7 | Zero if from gas or oil. 20-40% if formed from the starch sample. |

Example 2: Nanostarch Measurement

TABLE 2

Measurement of nanostarch by Scanning Electron Microscopy (SEM)

| Materials | Nanostarch size |
|---|---|
| Samples of Nanobioscrew | 25 nm |
| Surgical synthetic screw | 1-100 nm (Standard) |

The particle size of the nanostarch was measured by a Scanning Electron Microscopy (SEM), and the results indicate that the nanoparticle size of nanocomposite bio-thread biomaterial was 25 nm.

Example 3: Absorption Test (According to ASTM D570)

The nanobioscrews prepared were further evaluated for their ability to absorb moisture. The tests to determine water absorption were carried out in accordance with ASTM D570. The purpose of ASTM D570 is to determine the rate of water absorption by immersing the specimen (nanobioscrew) in water for a specific period of time. To perform the test, the nanobioscrews were dried in an oven for a specified time and temperature and then placed into a desiccator to cool. Immediately upon cooling, the nanobioscrews were weighed. The nanobioscrews were then submerged in water at of 23° C. for 48 hours. The nanobioscrews were removed, patted dry with a lint-free cloth, and weighed. Water absorption was calculated by determining the percentage increase in weight of the sample following the experiment to characterize this attribute. The results of this test are depicted in Table 3. It can be observed that the water absorption for the nanobioscrews prepared by the present disclosure is very low compared to surgical synthetic screws, which verifies their water-resistant property.

TABLE 3

Determination of water absorption by ASTM D570.

| Materials | Water absorption | Water absorption ASTM D570 |
|---|---|---|
| Nanobioscrew | 0.05% | — |
| Surgical synthetic screw | 0-0.16% | 0-0.16% |

Example 4: Burning Test

The nanobioscrews were burned using a gas burner. Odor, flame color, speed of burning, and spark were observed visually and compared with the surgical synthetic screws according to ASTM D3801 standard, published by ASTM International, West Conshohocken, Pennsylvania, United States of America. The results of this test are depicted in Table 4.

TABLE 4

Burning test according to the ASTM D3801

| Materials | Odor | Color of flame | Speed of burning | Spark or not |
|---|---|---|---|---|
| Nanobioscrew | Low odor | Yellow-orange | Slow | Spark |
| Surgical synthetic screw | Low odor | Yellow-orange | Slow | Spark |

Example 5: Color Test

Spray coating dye was used as the mode of application. It was attached properly to the nanobioscrew and dried after 1 h. The color dye drying time was 1.5 hours, which is less than the maximum of 2 hours, according to ASTM B117, published by ASTM International, West Conshohocken, Pennsylvania, United States of America. The results of this test are depicted in Table 5.

TABLE 5

Organic dye was used as the mode of application by ASTM B117

| Materials | Color Test (Drying Time) | ASTM B117 |
|---|---|---|
| Nanobioscrew | 45 min. | Maximum 2 hours |
| Surgical synthetic screw | 2 h (max.) | |

Example 6: Determination of Size and Shape Characteristics by ASTM A500

The nanobioscrews were hit by a hammer continuously for 2 minutes and pulled on for 5 min. There was no change in its shape and size as per the ASTM A500 standard test to compare with steel screws. The ASTM A500 standard is published by ASTM International, West Conshohocken, Pennsylvania, United States of America. The results of this study are depicted in Table 6.

TABLE 6

Size and shape characteristics

| Materials | Size and Shape | ASTM A 500 |
|---|---|---|
| Nanobioscrew | No swelling or shrinkage | Resistant Characters |
| Surgical synthetic screw | No swelling or shrinkage | |

Example 7: Energy Test

The energy was tested using the following equation: $E=1/2mv^2$ in accordance with the ASTM E1886 standard. The ASTM E1886 standard is published by ASTM International, West Conshohocken, Pennsylvania, United States of America. The results of this test are depicted in Table 7.

TABLE 7

Energy test of the nanobioscrew (ASTM E1886)

| Materials | Energy | ASTM E1886 |
|---|---|---|
| Nanobioscrew | 1.5 Joule | |
| Surgical synthetic screw | 1.0-25 Joule | |

Example 8: Firmness Test

The nanobioscrews were hit by a hammer of 1 kg. The hit was completed in 5 minutes. No bore or cracks were observed as per the ASTM D2925 or ASTM D5419 standard tests, respectively. The ASTM D2925 and ASTM D5419 standard tests are published by ASTM International, West Conshohocken, Pennsylvania, United States of America. The results of these tests are depicted in Table 8.

TABLE 8

Firmness test represented by a bore and crack test.

| Materials | Bore test ASTM D2925 | Crack test by ASTM D5419 |
|---|---|---|
| Nanobioscrew | No bore symptom | No crack symptom |
| Surgical synthetic screw | No bore symptom | No Crack symptom |

Example 9: Tensile Test

The tensile test was done by a Universal Test Machine for bioplastics according to the ASTM D5083 standard test. For this purpose, the nanobioscrews were placed in the grips of a Universal Test Machine at a specified grip separation and pulled until failure. For the ASTM D5083 test, the test speed was measured by the material specification. The default test speed was 5 mm/min (0.2 in/min), but modulus determination was made at 1.5 mm/min (0.057 in/min). A strain gauge was used to determine the elongation and tensile modulus. The maximum load capacity was 50 kN/m², depending upon the reinforcement and type. The ASTM D5083 standard is published by ASTM International, West Conshohocken, Pennsylvania, United States of America. The results of this test are depicted in Table 8.

TABLE 9

Determination of tensile test according to ASTM D5083

| Materials | Tensile strength (MPa/kg · m$^3$) | Tensile Modulus (GPa) |
|---|---|---|
| Nanobioscrews | 95.0 | 1.8 |
| Surgical synthetic screw | 70-230 (ASTM) | 1.0-3.0 (ASTM D5083) |

Example 10: Chemical Element Test

Chemical element tests of Ca, K, $CO_3^-$, Cl, Na, Si, Fe, Pb, Cu, Al, Sn & Zn were determined using the European Norm standardization. It has been seen that suitable results were exhibited as compared to the synthetic surgical screw. All the elements showed the values lower than the standard. The results of this test are depicted in Table 10.

TABLE 10

Determination of Chemical Element Test

| Chemical Elements (PPM) | Nanobioscrew (ppm) | Surgical Synthetic Screw |
|---|---|---|
| K | 10.5 ± 0.4$^b$ | 10 |
| Na | 5.1 ± 0.3b$^c$ | 5 |
| Cl | 0.57 ± 0.02$^d$ | 2 |
| $CO_3^-$ | 142 ± 1.0$^a$ | 440-5 |
| Ca | 9.0 ± 0.02$^a$ | 10 |
| Si | 3.0 | 5 |
| Fe | 1.5 | 5 |
| Pb | 0 | 5 |
| Cu | 0.3 | 5 |
| Al | 1 | 5 |
| Sn | 1.0 | 5 |
| Zn | 0.5 | 5 |

Mean ± standard error (SE, n = 3). Different letters indicate the significant difference at a 5% level of significance by LSD test.

A first aspect of the present disclosure describes an organic biodegradable nanocomposite for forming surgical implants. The organic biodegradable nanocomposite includes waste date seed nanoparticles present in an amount of about 15 wt. % to about 20 wt. %, pomegranate peel nanoparticles present in an amount of about 12 wt. % to about 16 wt. %, a polyvinyl chloride present in an amount of about 2 to about 5 wt. %, a polylactic glycolic acid present in an amount of about 2 to about 5 wt. %, an acrylate adhesive present in an amount of about 2 to about 5 wt. %, a starch including a mixture of pure starch present in an amount of about 7 wt. %, the pomegranate peel nanoparticles present in an amount of about 5 wt. % to about 10 wt. % and the date seed nanoparticles present in an amount of about 5 wt. % to about 10 wt. %, a waste coconut gel present in an amount of about 2 to about 5 wt. %, a waste okra gel present in an amount of about 2 wt. % to about 5 wt. %, a fresh gum (*Lannea* sp.) present in an amount of about 2 wt. % to about 5 wt. %, a waste aroid gum present in an amount of about 2 wt. % to about 5 wt. %, a chicken gut oil-based glycerin present in an amount of about 5 to about 10 wt. %, a dragon fruit peel dye present in an amount of about 5 wt. % to about 10 wt. %, a pomegranate peel organic dye present in an amount of about 5 wt. % to about 10 wt. %, a mangosteen peel organic dye present in an amount of about 3 wt. % to about 5 wt. %, and the balance is the camel knee bone nanoparticles, such that a total weight of the organic biodegradable nanocomposite is 100 wt. %. The wt. % is based on a total weight of the organic biodegradable nanocomposite.

In some aspects, the organic biodegradable nanocomposite includes pomegranate peel nanoparticles in an amount of about 14.1 wt. %.

In some aspects, the organic biodegradable nanocomposite includes waste date seed nanoparticles in an amount of about 18.8 wt. %.

In some aspects, the organic biodegradable nanocomposite includes the camel knee bone nanoparticles in an amount of about 14.1 wt. %.

In some aspects, the organic biodegradable nanocomposite includes the polylactic glycolic acid, the acrylate adhesive, and the starch in a total amount of about 17 wt. %; and the dragon fruit peel dye and the pomegranate peel organic dye in a total amount of about 12 wt. %.

In some aspects, the organic biodegradable nanocomposite includes polyvinyl chloride in an amount of about 3 wt. %, polylactic glycolic acid in an amount of about 3 wt. %, acrylate adhesive in an amount of about 3 wt. %, and the pure starch in an amount of about 7 wt. %.

In some aspects, the organic biodegradable nanocomposite includes the waste coconut gel in an amount of about 4 wt. %; the waste okra gel in an amount of about 3 wt. %; the fresh gum is present in an amount of about 3 wt %; the *Acacia nilotica* gum in an amount of about 3 wt. %; the waste aroid gel in an amount of about 5 wt. %; and the chicken gut oil-based glycerin in an amount of about 6 wt. %.

In some aspects, the organic biodegradable nanocomposite includes the dragon fruit peel dye in an amount of about 6 wt. %; and the pomegranate peel dye in an amount of about 6 wt. %.

In some aspects, the organic biodegradable nanocomposite is in the form of an organic bone screw obtained by extrusion molding the organic biodegradable nanocomposite into a mold.

In some aspects, the organic biodegradable nanocomposite is in the form of an organic bone plate obtained by injection molding the organic biodegradable nanocomposite into a mold and curing by heating.

In some aspects, the surgical implant is an organic dental post used for supporting a tooth implant.

A second aspect of the present disclosure describes a method 100 of making an organic biodegradable nanocomposite used for forming surgical implants. The method 100 comprises pyrolyzing, by an oven, an amount of a pomegranate peel, converting, by acid hydrolyzing in 88% hydrochloric acid, the pyrolyzed pomegranate peel to nanoparticles, grinding, in a grinder, an amount of date seeds to an average size ranging from 1 to 100 mm, converting, by acid hydrolysis in 88% hydrochloric acid, the ground date seeds to nanoparticles, converting, by acid hydrolysis in 90% hydrogen sulfate, camel knee bone to nanoparticles, and combining the pomegranate peel nanoparticles, the date seed nanoparticles and the camel knee bone nanoparticles with an organic polymer, a mixture of organic substances, and an organic dye.

In some aspects, the method 100 for making an implant includes filling a mold for a bone screw with the organic biodegradable nanocomposite; curing the mold; removing the bone screw from the mold; and washing the bone screw with a solvent.

In some aspects, the method 100 for making an implant comprises filling a mold for a surgical compression plate with the organic biodegradable nanocomposite; curing the mold; removing the organic surgical compression plate from the mold; and washing the surgical compression plate with a solvent.

In some aspects, the method 100 for making a dental implant comprises filling a mold for an organic dental prosthesis with the organic biodegradable nanocomposite; curing the mold; removing the organic dental prosthesis from the mold; and washing the organic dental prosthesis with a solvent.

In some aspects, the method 100 for making an organic implant comprises curing, in an oven, the organic biodegradable nanocomposite; and sculpturing the surgical implant from the cured organic biodegradable nanocomposite.

In some aspects, the method 100 for making an organic biodegradable nanocomposite comprises forming a mixture, in a blender, of about 14.1 wt. % of the pomegranate peel nanoparticles, about 18.8 wt. % of the date seed nanoparticles and about 14.1 wt. % of the camel knee bone nanoparticles.

In some aspects, the method 100 for making an organic biodegradable nanocomposite comprises combining with an organic polymer, which further comprises adding, into the mixture, about 3 wt. % of a polyvinyl chloride, about 3 wt. % of a polylactic glycolic acid, about 3 wt. % of an acrylate adhesive and about 7 wt. % of a pure starch.

In some aspects, the method 100 of making the organic biodegradable nanocomposite comprises combining the pomegranate peel nanoparticles, the date seed nanoparticles and the camel knee bone nanoparticles with a mixture of organic substances by mixing in about 4 wt. % of a coconut gel, mixing in about 3 wt. % of an okra gel; mixing in about 3 wt. % of a natural glue made from fresh gum of a *Lannea* species; mixing in about 3 wt. % of an *Acacia nilotica* gum; mixing in about 5 wt. % of an aroid gel; and mixing in about 6 wt. % of an oil-based glycerin derived from chicken gut.

In some aspects, the method 100 for making an organic biodegradable nanocomposite comprises combining the pomegranate peel nanoparticles, the date seed nanoparticles, and the camel knee bone nanoparticles with a mixture with an organic dye by mixing in about 6 wt. % of a dragon fruit peel dye and mixing in about 6 wt. % of a pomegranate peel organic dye.

Numerous modifications and variations of the present disclosure are possible in light of the above teachings. It is, therefore, to be understood that within the scope of the appended claims, the invention may be practiced otherwise than as specifically described herein.

The invention claimed is:

1. An organic biodegradable nanocomposite suitable for forming surgical implants, comprising, relative to total nanocomposite weight:
a polyvinyl chloride in a range of from 2 to 5 wt. %;
a polylactic glycolic acid in a range of from 0.2 to 5 wt. %;
an acrylate adhesive in a range of from 2 to 5 wt. %; and
a mixed starch comprising (a) pure starch present in 7 wt. %, (b) a waste date seed nanoparticle starch in a range of from 15 to 20 wt. %, and (c) a pomegranate peel nanoparticle starch in a range of from 12 to 16 wt. %;
a waste coconut gel in a range of from 2 to 5 wt. %;
a waste okra gel in a range of from 2 to 5 wt. %;
a fresh gum obtained from *Lannea* sp. in a range of from 2 to 5 wt. %;
an *Acacia nilotica* gum in a range of from 2 to 5 wt. %;
a waste aroid gel in a range of from 2 to 5 wt. %;
a chicken gut oil-based glycerin in a range of from 5 to 10 wt. %;
a dye comprising (i) a dragon fruit peel organic color extract in a range of from 5 to 10 wt. %, (ii) a pomegranate peel organic color extract in a range of from 5 to 10%, and optionally (iii) a mangosteen peel organic color extract in a range of from 3 to 5%; and
a balance of camel knee bone nanoparticles.

2. The nanocomposite of claim 1, wherein the pomegranate peel nanoparticles starch is present in 14.1 wt. %.

3. The nanocomposite of claim 1, wherein the waste date seed nanoparticles starch is present in 18.8 wt. %.

4. The nanocomposite of claim 1, wherein the camel knee bone nanoparticles are present in 14.1 wt. %.

5. The nanocomposite of claim 1, wherein: a total amount of the polyvinyl chloride, the polylactic glycolic acid, the acrylate adhesive and the starch is 17 wt. %; and a total amount of the dragon fruit peel organic color extract, the pomegranate peel organic color extract, and the mangosteen peel organic color extract is 12 wt. %.

6. The nanocomposite of claim 5, wherein:
the polyvinyl chloride is present in 3 wt. %;
the polylactic glycolic acid is present in 3 wt. %;
the acrylate adhesive is present in 3 wt. %; and
the pure starch is present in 7 wt. %.

7. The nanocomposite of claim 1, wherein:
the waste coconut gel is present in 4 wt. %;
the waste okra gel is present in 3 wt. %;
the fresh gum is present in 3 wt. %;
the *Acacia nilotica* gum is present in 3 wt. %;
the waste aroid gel is present in 5 wt. %; and
the chicken gut oil-based glycerin is present in 6 wt. %.

8. The nanocomposite of claim 1, wherein:
the dragon fruit peel organic color extract is present in 6 wt. %; and
the pomegranate peel organic color extract is present in 6 wt. %.

9. The nanocomposite of claim 1, further comprising:
an organic bone screw obtained by extrusion molding the nanocomposite into a mold.

10. The nanocomposite of claim 1, further comprising:
an organic bone plate obtained by injection molding the nanocomposite into a mold and curing by heating.

11. The nanocomposite of claim 1, wherein the surgical implant is an organic dental post used for supporting a tooth implant.

12. A method making an organic biodegradable nanocomposite used in forming a surgical implants, the method comprising:
pyrolyzing, by an oven, an amount of pomegranate peel;
converting, by acid hydrolysis in 88% hydrochloric acid, the pyrolyzed pomegranate peel to nanoparticles;
grinding, in a grinder, an amount of date seeds to an average size in a range of from 1 to 100 mm;
converting, by acid hydrolysis in 88% hydrochloric acid, the ground date seeds to nanoparticles;
converting, by acid hydrolysis in 90% sulfuric acid, camel knee bone to nanoparticles;
combining the pomegranate peel nanoparticles, the date seed nanoparticles, and the camel knee bone nanoparticles with:
an organic polymer;
a mixture of organic substances; and
an organic dye.

13. The method of claim 12, further comprising:
filling a mold for an organic bone screw with the nanocomposite;
curing the mold;
removing the organic bone screw from the mold; and
washing the organic bone screw with a solvent.

14. The method of claim 12, further comprising:

filling a mold for an organic surgical compression plate with the nanocomposite;
curing the mold;
removing the organic surgical compression plate from the mold; and
washing the organic surgical compression plate with a solvent.

15. The method of claim 12, further comprising:
filling a mold for an organic dental prosthesis with the nanocomposite;
curing the mold;
removing the organic dental prosthesis from the mold; and
washing the organic dental prosthesis with a solvent.

16. The method of claim 12, further comprising:
curing, in an oven, the nanocomposite; and
sculpturing the surgical implant from the cured nanocomposite.

17. The method of claim 12, wherein the combining comprises:
forming a mixture, in a blender, 14.1 wt. % of pomegranate peel nanoparticles, 18.8 wt. % of date seed nanoparticles and 14.1% wt. % of the camel knee bone nanoparticles.

18. The method of claim 17, wherein the combining with an organic polymer further comprises:
adding, into the mixture, 3 wt. % of a polyvinyl chloride, 3 wt. % of a polylactic glycolic acid, 3 wt. % of an acrylate adhesive, and 7 wt. % of a starch.

19. The method of claim 18, wherein the combining with a mixture of organic substances further comprises:
mixing in about 4 wt. % of a coconut gel;
mixing in 3 wt. % of an okra gel;
mixing in 3 wt. % of a natural glue made from fresh gum of a *Lannea* species;
mixing in 3 wt. % of an *acacia nilotica* gum;
mixing in 5 wt. % of an aroid gel; and
mixing in 6 wt. % of an oil-based glycerin derived from chicken gut.

20. The method of claim 19, wherein the combining with an organic dye comprises:
mixing in 6 wt. % of a dragon fruit peel organic color extract; and
mixing in 6 wt. % of a pomegranate peel organic color extract.

* * * * *